United States Patent [19]

Miripol et al.

[11] Patent Number: 4,726,949

[45] Date of Patent: Feb. 23, 1988

[54] IRRADIATION OF BLOOD PRODUCTS

[75] Inventors: Jeffrey E. Miripol, Evanston; Arnold Bilstad, Deerfield; John Foley, Wheeling; Dean Glash, McHenry, all of Ill.

[73] Assignee: Baxter Travenol Laboratories, Inc., Deerfield, Ill.

[21] Appl. No.: 900,217

[22] Filed: Aug. 26, 1986

[51] Int. Cl.$^4$ .............................................. A61K 35/14
[52] U.S. Cl. ........................................ 424/101; 435/2
[58] Field of Search ............................ 424/101; 435/2

[56] References Cited

U.S. PATENT DOCUMENTS 4,608,255  8/1986  Kahn et al. .................... 424/101
4,612,007  9/1987  Edelson .

OTHER PUBLICATIONS

Bredberg et al–Chem. Abst., vol. 101 (1984), p. 146,941h.
Langner et al–Chem. Abst., vol. 88 (1978), p. 31915y.
Lynch et al.–Chem. Abst., vol. 99 (1983), p. 172086t.
Krylenkov et al–Chem. Abst., vol. 101 (1984), p. 206,812d.

*Primary Examiner*—Sam Rosen
*Attorney, Agent, or Firm*—Paul C. Flattery; Garrettson Ellis; Bradford R. L. Price

[57] ABSTRACT

A thin film of white blood cells is irradiated with ultraviolet radiation predominately of a wavelength of 280 to 320 nanometers, and preferably at an intensity of 4 to 15 milliwatts per square cm. At such a radiation intensity it is not necessary to agitate the thin film of white blood cells to accomplish the purposes of this invention. The white blood cells so processed substantially lose their capability to set off an immune reaction in an alloimmunized patient. The white blood cells may preferably be placed into such film in a flat, flexible bag made of poly(ethylene-vinyl acetate) plastic, with the flat, flexible bag being stretched in a direction normal to the path of ultraviolet radiation.

18 Claims, 3 Drawing Figures

IRRADIATION OF BLOOD PRODUCTS

TECHNICAL FIELD

In Kahn U.S. patent application Ser. No. 696,657, filed Jan. 31, 1985, now U.S. Pat. No. 4,608,255, and entitled: A Biocompatible Method for In Situ Production of Functional Platelets Lacking in Immunogenicity, it is taught to expose platelet preparations to ultraviolet (U.V.) radiation, to eliminate or greatly decrease an immune response to the platelet preparation by alloimmunized patients. As observed by Dr. Kahn, it is generally believed that this alloimmunization is caused by the passenger lymphocytes present in the platelet concentrates prepared by a standard procedure.

The effect of such an alloimmunization reaction is that donated platelets are quickly removed from the bloodstream of a patient, so that the beneficial, life saving effect of administered platelets may eventually become unavailable to patients in serious need of it, despite frequent infusions of platelets to such a patient.

As taught by Dr. Kahn, the alloimmunization of a patient comes from repeated platelet transfusions, as may be necessary for cancer patients undergoing chemotherapy or the like.

The Kahn patent application teaches placing a platelet suspension in a plastic container which is permeable to ultraviolet radiation. Specifically, a dosage of radiation of about 645 Joules per square meter for about 10 to 40 minutes is proposed, using polyethylene, polypropylene, or polyvinyl chloride bags. The ultraviolet radiation passes through the bag walls to irradiate platelets and other cells present, to provide a cell preparation for administration to a patient which elicits little or no immune response from patients who have been alloimmunized to such platelet preparations.

While the Kahn method restores to alloimmunized patients the life saving benefits of platelet therapy, certain disadvantages are found. In the actual work of Kahn upon which the Kahn patent application was based, it has turned out to be necessary or at least highly desirable to agitate the platelet preparation while they are being irradiated. Otherwise, incomplete results are achieved. Additionally, while Kahn suggests the use of several different plastic materials for use in his cell irradiation process, one particular plastic formulation provides additional advantages above and beyond the teachings of Kahn, when used in accordance with this present application.

Accordingly, the improvements provided by the invention of this application produce a significantly improved method for treating white blood cells so as to permit their effective use in alloimmunized patients. Specifically, agitation of the cells during irradiation is not required. A superior, U.V. "B" transparent bag material is provided, and the blood cell preparations may be irradiated for shorter periods of time, while achieving substantially equal benefits to those provided by the process of Dr. Kahn.

DESCRIPTION OF THE INVENTION

In accordance with this invention, a thin film of blood product, such as platelet concentrates, typically with white cell contamination, is irradiated with ultraviolet radiation predominately of a wavelength of 280 to 320 nanometers and at an intensity of 4 to 15 and preferably 7 to 11 milliwatts per square cm., typically without agitation of the film, to provide a total energy exposure of typically 800 to 2800 millijoules per square cm. of ultraviolet radiation, and preferably 1600 to 2500 millijoules per square cm. As the result of this, the white blood cells present in the blood product substantially lose their capability to set off an immune reaction in an alloimmunized patient. Excessive U.V. energy exposure is generally deleterious to the blood product, while not enough U.V. energy does not reduce the lymphocyte stimulatory activity to a sufficient degree.

In accordance with this invention, the exposure of the blood to ultraviolet radiation of the wavelength and intensity as specified above typically eliminates the need for agitation of the film. Typically also, the length of the irradiation process may be from 0.25 to 15 minutes long, which, due to increased intensity, when compared with the Kahn et al. work, provides a shorter processing time.

Preferably, the white blood cells are irradiated while occupying a flat, flexible bag made of poly(ethylene-vinyl acetate) plastic. This material is highly transparent to ultraviolet radiation; retains its strength at cryogenic temperatures if the cells are to be stored under cryogenic conditions; is easily fabricated by heat sealing into flat, flexible bags; and exhibits the high oxygen permeability through the bag wall which is desired for a container for storing platelets or the like. Typically, the thin film of blood product, such as platelet concentrate contaminated with white blood cells, is from 0.1 to 5 cm. thick during the irradiation step. It is also typical for the flat, flexible bag used in this process, and made out of poly(ethylene-vinyl acetate) plastic, to contain from 10 to 30 weight percent of vinyl acetate units, with the balance being ethylene units, such bag preferably having a wall thickness of 0.005 to 0.025 inch.

It is also preferable in accordance with this invention to stretch the flat, flexible bag in at least one direction which is normal to the direction of ultraviolet radiation, to help define the thin film of blood product with the bag.

The term "white blood cells" is intended to include the general class of leukocytes, including mononuclear cells and neutraphils, lymphocytes, and any other cells found in the blood, above and beyond red cells and platelets. It is to be understood that the blood product processed in this invention may, and usually does include. platelets and/or red cells. Also, substantially cell-free products having some white cells may be treated by this invention. Likewise, whole blood may be irradiated in accordance with the invention, or any other fraction thereof.

It is generally desired to use high intensity ultraviolet bulbs, with specific output in the UV-B wavelength range, for the process of this invention. Not all ultraviolet bulbs are capable of providing sufficient intensity for the purposes of this invention. Also, some ultraviolet bulbs emit much energy at a wavelength of 254 nanometers, and are not as effective in providing the desired effect as the somewhat longer wavelength ultraviolet radiation used in this invention. In addition, 254 nanometer energy causes damage to blood cells. Also, bulbs providing energy in the UV-A range (about 365 nanometers) do not provide good reduction of the lymphocyte alloimmunization effect.

Flexible, collapsible bags made of poly(ethylene-vinyl acetate) (E.V.A.) plastic are commercially available from the Fenwal Division of Baxteer Travenol Laboratories, Inc. of Deerfield, Ill.

DESCRIPTION OF SPECIFIC EMBODIMENTS

Figure 1:
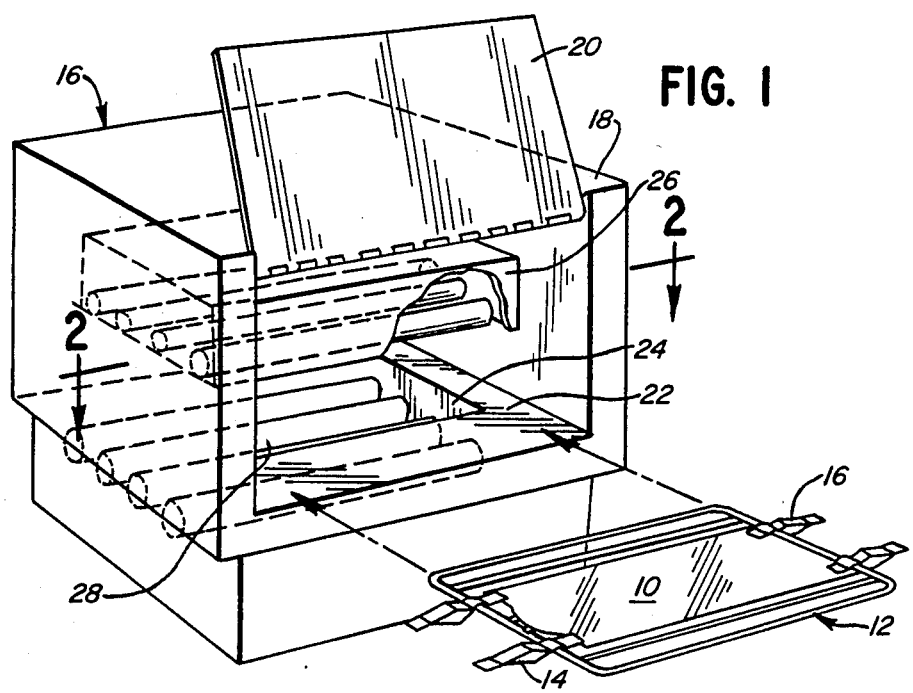
FIG. 1 is a perspective view of an irradiation device which is in the process of receiving a stretched, plastic container of platelets mixed with white blood cells.
Figure 2:
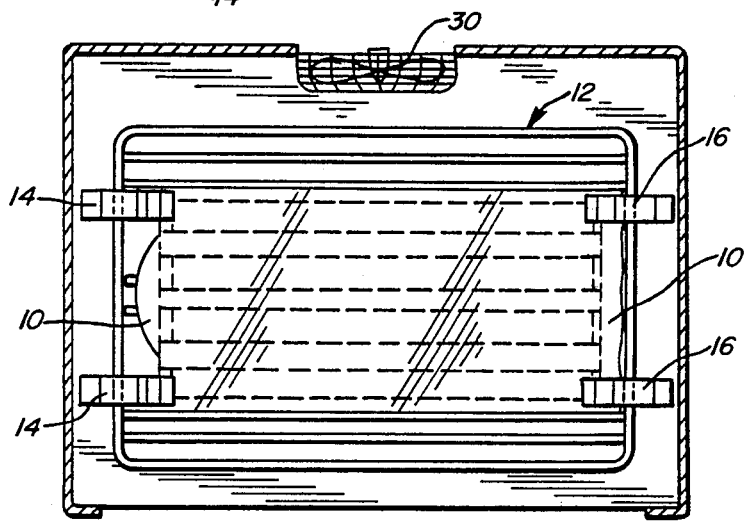
FIG. 2 is a sectional view taken along line 2—2 of FIG. 1, showing the plastic bag carried in its stretching device and positioned for irradiation inside the radiation apparatus.

Referring to FIGS. 1 and 2, a flexible, collapsible bag 10 is provided, holding a unit of platelets which have been collected by conventional centrifugal processing of freshly collected whole blood, or by on-line apheresis collection of platelet products.

In FIG. 2, bag 10 is carried upon a framework 12 of metal rods which are welded together at the corners. As shown, the ends of collapsible bag 10 are retained by spring clips 14, 16, to hold the bag in stretched condition. The effect of this is to cause the thickness of the platelet preparation within bag 10 to be minimized, and to be made relatively uniform, so that the dosage of ultraviolet radiation received by the individual portions of the platelet preparation is rather constant. Biaxial stretching of bag 10 may also be used if desired.

U.V. radiation device 16 defines a casing 18, a sliding door 20, and interior rack 22. Rack 22 is provided centrally in the device with an aperture 24, which is preferably sized so that the entire bag 10 may be placed over said aperture, with clips 14, 16, resting upon rack 22 to support bag 10 over aperture 24.

In this particular embodiment, device 16 defines an upper light fixture 26, and lower light fixture 28. The specific lights used, and the electronic circuitry controlling such use, may be entirely conventional, utilizing typically commercially available high intensity bulbs such as eight bulbs purchased from Spectronics Corp., Westbury, N.Y. (such as model BLE-1T158). Also, exhaust fan 30 may be provided in the back of casing 18 to exhaust the heat generated by bulb assemblies 26, 28.

The device is designed so that platelets (or other blood products treated with this system) do not become heated above 31 degrees C. Prolonged heating of such above 31 degrees C. is deleterious to their function.

In operation, the individual bags 10, typically of platelets (plus a few lymphocytes, which are supsected as being the prime contributors to the alloimmunization process), are stretched in framework 12, and inserted horizontally into ultraviolet application chamber so that bag 10 rests over aperture 24. Sliding door 20 is closed, and the thin film of platelets contaminated with white blood cells within stretched bag 10 is irradiated with ultraviolet radiation, typically with a wavelength of predominately 300 to 320 nanometers, having a maximum emission of about 300-310 nanometers. No means for agitating the bag is necessary in order to achieve the desired purpose of this invention of causing the white blood cells to lose their potential to set off an immune reaction in an alloimmunized patient.

Specifically, the thickness of the film of blood product within bag 10 is about 4 cm. thick, with a typical bag 10 having a wall thickness of about 0.015 inch, and being made of E.V.A. having about 18 weight percent of vinyl acetate units, the balance being ethylene units. Typically, the intensity of the ultraviolet radiation is about 9 milliwatts per square cm., and the irradiation process may have a duration of about 4 minutes, to provide about 2200 millijoules per square cm.

After the irradiation step is complete, ultraviolet light assemblies 26, 28, may be shut off; door 20 may be opened; and bag 10 with its attached framework 12 removed. Bag 10 is then easily removed from spring clips 14, 16, and placed under conventional storage conditions until use with a patient is desired. Immediately thereafter, or at any other desired time, another bag 10 may be stretched into framework 12, and the process may be repeated, to provide white blood cells, and especially platelet-containing solutions, which do not set off an alloimmune reaction in patients.

Figure 3:
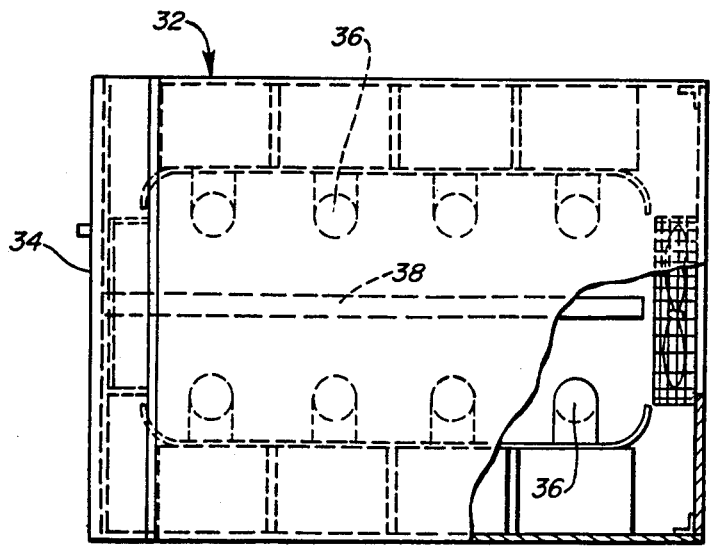
FIG. 3 is a plan view, with portions broken away, of another embodiment of apparatus utilized to perform the method of this application.

Turning to FIG. 3, the plan view of a bag irradiation device is shown, having casing 32 and door 34, into which assemblies of framework 12 and cell-containing bags 10 may be inserted. In this particular design, ultraviolet bulbs 36 may be vertically mounted on both sides of a sliding track 38 into which framework 23 can slidingly be fit and travel into and out of irradiation device 32.

In this embodiment, bag 10 may be placed with its longer axis of width extending vertically, to be parallel to the axes of U.V. bulbs 36, which are of cylindrical shape, shown in cross section in FIG. 3.

Upon installation of framework 12 and bag 10 within the structure of FIG. 3, door 34 may be closed and lights 36 actuated to provide light of 280 to 320 nanometers and at a typical intensity of about 9 milliwatts per square cm.

No apparatus for agitating the white blood cells within bag 10 is provided in this embodiment either, since it has been found that irradiation at the wavelength and intensity as specified above can provide sufficient irradiation to the blood cells in a stretched bag carrying a unit of such cells, without agitation.

The E.V.A. bags preferably used in this invention have the added desirable feature in that they may be free of leachable materials. This reduces the amount of undesired and uncontrolled materials which find their way into the white cell preparations during processing.

Continuous ultraviolet irradiation processes may be used as well, with the bags lying on a conveyor belt, either with or without stretching as provided by framework 12, to be carried across a source of ultraviolet radiation. The ultraviolet radiation may come from only one direction, using a single ultraviolet light assembly, or a plurality of such light assemblies may be provided, above or below, and/or from side-to-side of such conveyor belt. Alternatively a series of ultraviolet sources may be provided in-line sequentially to expose the containers to the desired level of ultraviolet radiation.

Additionally, a safety interlock may be provided by conventional means to prevent activation of the ultraviolet lights while the door of either casing 16 or 32 is open. Additionally, electronic circuitry is known for causing the ultraviolet lights to be activated until a desired overall integrated exposure is reached, and then causing the ultraviolet bulbs to shut off when such exposure is reached. Such as exposure control system operates independently of time and intensity, and may be used in this invention if desired.

Alternatively, bag 10 may be squeezed with a U.V.-transparent plate (e.g. quartz), or a screen, rather than stretching, to achieve a uniform, thin film during irradiation.

The above has been offered for illustrative purposes only, and is not intended to limit the scope of the invention of this application, which is as defined in the claims below.

That which is claimed is:

1. The method of treating white blood cells comprising irradiating a thin film of a blood product containing white blood cells with ultraviolet radiation predominately of a wavelength of 280 to 320 nanometers at an intensity of 4 to 15 milliwatts per square cm., to provide a total energy exposure of 800 to 2800 millijoules per square cm. of ultraviolet radiation for a sufficient time, whereby said white blood cells substantially lose their capability to set off an immune reaction in an alloimmunized patient.

2. The method of claim 1 in which said blood product is irradiated while occupying a flat, flexible bag made of poly(ethylene-vinyl acetate) plastic.

3. The method of claim 2 in which said plastic contains from 10 to 30 weight percent by weight of vinyl acetate units and said bag has a wall thickness of 0.005 to 0.025 inch.

4. The method of claim 1 in which said thin film of blood product is from 0.1 to 5 cm. thick.

5. The method of claim 1 in which said irradiation is from 0.25 to 15 minutes long.

6. The method of claim 1 in which said blood product is irradiated while occupying a flat, flexible bag which is stretched during said irradiation to define said thin film of blood product within said bag.

7. The method of claim 1 in which said total energy exposure is 1600 to 2500 millijoules per square cm.

8. The method of claim 1 in which said intensity is 7 to 11 milliwatts per square cm.

9. The method of claim 1 in which said irradiating takes place without agitation of the thin film.

10. The method of claim 1 in which said ultraviolet radiation is predominately of a wavelength of 300 to 320 nanometers.

11. The method of treating white blood cells comprising irradiating a thin film of blood product containing white blood cells with ultraviolet radiation predominately of a wavelength of 280 to 320 nanometers, which comprises: presenting said blood product to the radiation while said blood product occupies a flat, flexible bag made of poly(ethylene-vinyl acetate) plastic, said plastic containing from 10 to 30 percent of vinyl acetate units, and said bag having a wall thickness of 0.005 to 0.025 inch, whereby said white blood cells substantially lose their capability to set off an immune reaction in an aloimmunized patient.

12. The method of claim 11 in which said bag is axially stretched during said irradiation to define said think film of blood product within said bag.

13. The method of claim 12 in which said thin film of white blood cells is from 0.1 to 5 cm. thick.

14. The method of treating white blood cells comprising irradiating a thin film of blood product containing white blood cells with ultraviolet radiation predominately of a wavelength between 280 to 320 nanometers at an intensity of 7 to 11 milliwatts per square cm., without agitation of the film, to provide a total energy exposure of 800 to 2800 millijoules per square cm. of ultraviolet radiation, in which said blood product is irradiated while occupying a flat, flexible bag which is stretched during said irradiation to define said thin film of white blood cells within said bag, said bag being made of poly(ethylene-vinyl acetate) plastic.

15. The method of claim 14 which said plastic contains from 10 to 30 weight percent of vinyl acetate units, and said bag has a wall thickness of 0.005 to 0.025 inch.

16. The method of claim 14 in which said irradiation is from 0.25 to 15 minutes long.

17. The method of claim 14 in which said thin film of white blood cells is from 0.1 to 5 cm. thick.

18. The method of claim 15 in which the total energy exposure of ultraviolet radiation applied is 1600 to 2500 millijoules per square cm.$^2$.

* * * * *